United States Patent [19]

Sagae

[11] Patent Number: 5,176,637
[45] Date of Patent: Jan. 5, 1993

[54] CATHETER EQUIPPED WITH A DILATION ELEMENT

[75] Inventor: Kyuta Sagae, Kanagawa, Japan

[73] Assignee: Terumo Kabushiki Kaisha, Tokyo, Japan

[21] Appl. No.: 873,348

[22] Filed: Apr. 21, 1992

Related U.S. Application Data

[63] Continuation of Ser. No. 688,044, Apr. 19, 1991, abandoned.

[30] Foreign Application Priority Data

Apr. 19, 1990 [JP] Japan .................................... 103943

[51] Int. Cl.⁵ .......................................... A61M 29/00
[52] U.S. Cl. ..................................... 604/96; 604/283; 606/192
[58] Field of Search ................................. 604/96–104, 604/280, 283, 53; 606/191–194

[56] References Cited

U.S. PATENT DOCUMENTS

| | | |
|---|---|---|
| 4,323,071 | 4/1982 | Simpson et al. |
| 4,917,666 | 4/1990 | Solar et al. |
| 4,955,895 | 9/1990 | Sugiyama et al. |
| 4,964,853 | 10/1990 | Sugiyama et al. |
| 4,998,917 | 3/1991 | Gaiser et al. ........................... 604/96 |
| 4,998,923 | 3/1991 | Samson et al. .................... 604/96 X |
| 5,035,694 | 7/1991 | Kasprzyk et al. ...................... 604/96 |

FOREIGN PATENT DOCUMENTS

| | | |
|---|---|---|
| 0318918 | 6/1989 | European Pat. Off. |
| 2380786 | 9/1978 | France |
| 1566674 | 2/1978 | United Kingdom |
| 88/06464 | 9/1988 | World Int. Prop. O. |
| 89/08471 | 9/1989 | World Int. Prop. O. |

Primary Examiner—John D. Yasko
Attorney, Agent, or Firm—Frishauf, Holtz, Goodman & Woodward

[57] ABSTRACT

A catheter equipped with a dilatation element comprising, an inner tube having a first lumen open at the distal end, an outer tube which surrounds the inner tube so that a predetermined length of the distal end of the inner tube extends out of the distal end of the outer tube and a second lumen is formed between the outer surface and the inner tube, a foldable dilatation element which has the front and rear end portions attached to the inner tube and the outer tube respectively and whose internal space communicates with the second lumen, a first opening which communicates with the first lumen at the proximal end of the inner tube, and a second opening which communicates with the second lumen at the proximal end of the outer tube, and characterized in that a portion near the distal end of the outer tube is fixed to the inner tube without blocking the second lumen.

11 Claims, 5 Drawing Sheets

CATHETER EQUIPPED WITH A DILATION ELEMENT

This application is a continuation of application Ser. No. 07/688,044, filed Apr. 19, 1991 now abandoned.

FIELD OF THE INVENTION

The present invention relates to a catheter equipped with a dilatation element for treating stenosis of blood vessels by dilating the stenotic sections and restoring the blood stream to the peripheral side of those sections.

BACKGROUND OF THE INVENTION

As a catheter equipped with a dilatation element for dilating stenotic sections in blood vessels, so called Simpson-Robert type catheter disclosed in the specification of U.S. Pat. No. 4,323,071 is used.

The stenotic lesions in blood vessels which could be treated by the early models of this type of catheter were limited to those in the proximity of the coronary arteries anatomically, of about 15 to 20 mm in length, localized in a single branch, and not calcificated. But improved in order to expand the treatable lesions, later models have become able to treat more serious stenotic lesions such as sub-total obliteration and at more peripheral-side vessels.

The applicant of this application has previously proposed another catheter which comprises an inner tube, an outer tube disposed coaxial in the inner tube, and a dilatation element attached to the inner and outer tubes, as described in International Publication No. W088/6464.

In the Simpson-Robert type catheter described in U.S. Pat. No. 4,323,071 and the one disclosed in the International Publication No. W088/6464, the inner and outer tubes are fixed at their proximal ends, while the rear end of a dilatation element is attached to the distal end of the outer tube and the front end to the distal end of the inner tube. The outer and inner tubes are thus connected by the intermediary of the dilatation element at their distal ends.

The coaxial-type catheters as disclosed in U.S. Pat. No. 4,323,071 and in the International Publication No. W088/6464 are inserted into vessels with the dilatation element folded up around the inner tube. While being advanced in vessels, a small displacement of the relative position of the outer and inner tubes can occur due to the frictional resistance exerted over the dilatation element and the force from the inner wall of blood vessels against the inner tube when the tip of the inner tube is in contact with the vessel wall. This displacement between the outer and inner tubes pulls or pushes the ends o the folded dilatation element. This force can cause the deformation of the dilatation element and sometimes the dilatation element expands thicker in the outer diameter than in its completely folded state. In that case, manipulation of the catheter, particularly insertion of the dilatation element into stenotic sections becomes difficult.

SUMMARY OF THE INVENTION

The object of this invention is to solve the above problems and provide a new and improved catheter equipped with a dilatation element which can prevent the slight displacement of the relative position of the inner and outer tube while being advanced in blood vessels and hence the undesirable expansion of the dilation element caused by the displacement and thereby makes easier the manipulation of the catheter, particularly the insertion of the distal end of the catheter into stenotic sections in blood vessels.

The above objects are attained by the catheter comprising, an inner tube having a first lumen open at the distal end, an outer tube which surrounds the inner tube so that a predetermined length of the distal end of the inner tube extends out of the distal end of the outer tube and a second lumen is formed between the inner surface of the outer tube and the outer surface of the inner tube, a foldable dilatation element which has the front and rear end portions attached to the inner tube and the outer tube respectively and whose internal space communicates with the second lumen, a first opening which communicates with the first lumen at the proximal end of the inner tube, and a second opening which communicates with the second lumen at the proximal end of the outer tube, a fixing member inserted between the outer tube and the inner tube at a position a certain distance from the distal end of the outer tube toward the proximal end, the outer tube is fixed to the inner tube without blocking the second lumen by the fixing member, and the distal end portion of the outer tube is not fixed to the inner tube.

DETAILED DESCRIPTION OF THE PREFERRED EMBODIMENTS

Figure 1:
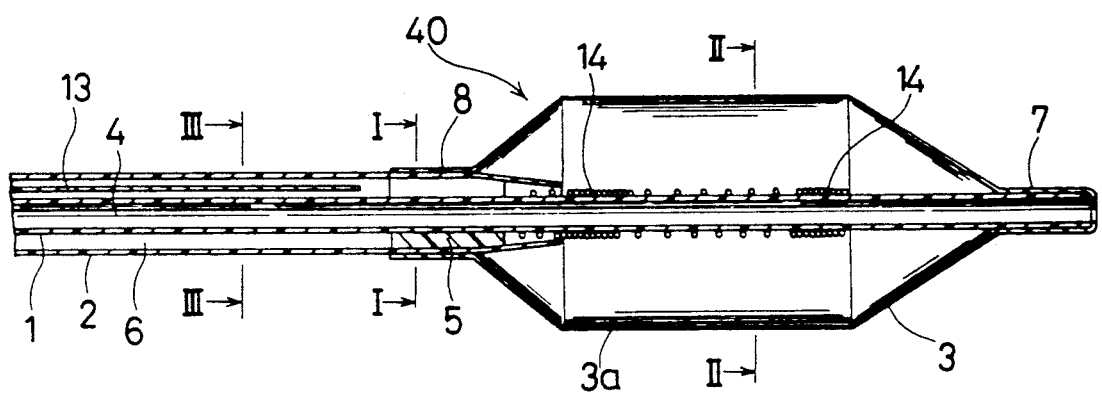
FIG. 1 is an enlarged cross-sectional view of the distal region of an embodiment of the catheter equipped with a dilatation element according to the present invention.
Figure 3:
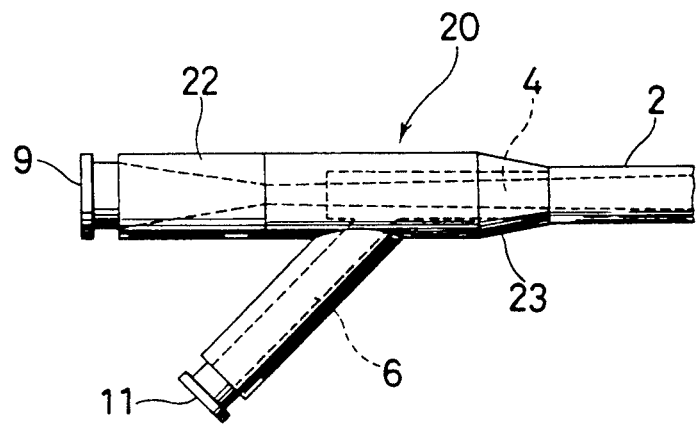
FIG. 3 shows the proximal region of an embodiment of the catheter equipped with a dilatation element according to the present invention.

FIG. 1 shows a cross-section of the distal region of an embodiment of the catheter equipped with a dilatation element according to the present invention and FIG. 3 shows the proximal region of the catheter.

The catheter equipped with a dilatation element of the present invention 40 comprises an inner tube 1 having a first lumen 4 open at the distal end; an outer tube 2 which encases the inner tube 1 so that a predetermined length of the distal end portion of the inner tube 1 extends out of the distal end of the outer tube and a second lumen 6 is formed between the inner surface of the outer tube 2 and the outer surface of the inner tube 1; a foldable dilatation element 3 which has the front end portion 7 and the rear end portion 8 attached to the inner tube 1 and the outer tube 2 respectively and whose internal space is connected with the second lumen 6 near the rear end portion; a first opening 9 which is connected to the first lumen 4 at the proximal end of the inner tube 1; and a second opening 11 which is communicated with the second lumen 6 at the proximal end of the outer tube 2. A portion near the distal end of the outer tube 2 is fixed to the inner tube 1 without blocking the second lumen 6.

The proximal ends of the outer and inner tubes 1 and 2 are inserted into a branched hub 20 and held securely. The first and second openings 9 and 11 are formed in the branched hub 20. The first lumen 4 is a pass for inserting a guide wire and its proximal end is connected with the opening 9 which serves as a guide wire port.

The inner tube has an outer diameter ranging from 0.30 to 2.50 mm, preferably 0.40 to 2.40 mm and an inner diameter ranging from 0.20 to 2.35 mm, preferably 0.25 to 1.80 mm.

The material preferable for forming the inner tube 1 has a certain amount of flexibility. The materials usable for the inner tube 1 are thermoplastic resins such as polyolefin (polyethylene, polypropylene, ethylene-propylene copolymer, ethylene-vinyl acetate copolymer, etc.), polyvinyl chloride, polyamide elastomer and polyurethane. Of the above materials, the olefin resins are more preferable.

Figure 5:
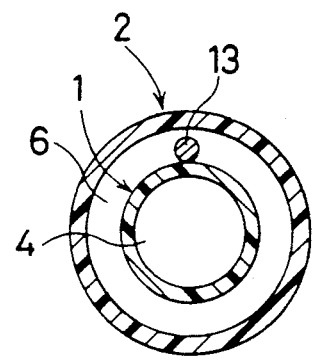
FIG. 5 is a cross-sectional view taken along the line III—III in FIG. 1.

The outer tube 2 surrounds the inner tube 1 so that a predetermined length of the distal end portion of the inner tube 1 extends out of the outer tube. As shown in FIG. 5 which is a cross-sectional view taken along the line III—III in FIG. 1, the second lumen 6 is formed between the inner surface of this outer tube 2 and the outer surface of the inner tube 1 and thus has a sufficient capacity. The distal end of the second lumen 6 is connected with the rear end portion of the internal space of the dilatation element 3 hereinafter described. The proximal end of the second lumen 6 is connected with the second opening 11 formed in the branched hub 20 which is an injection port for injecting a fluid such as a radiographic contrast medium to expand the dilatation element 3.

Figure 2:
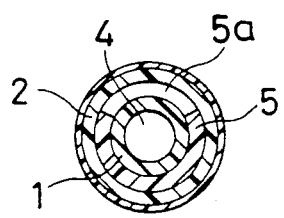
FIG. 2 is a cross-sectional view taken along the line I—I in FIG. 1.
Figure 7:
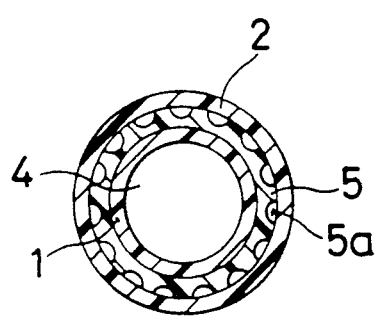
FIGS. 7 and 8 are a cross-sectional view of other embodiments of the catheter equipped with a dilatation element according to the present invention, respectively.
Figure 8:
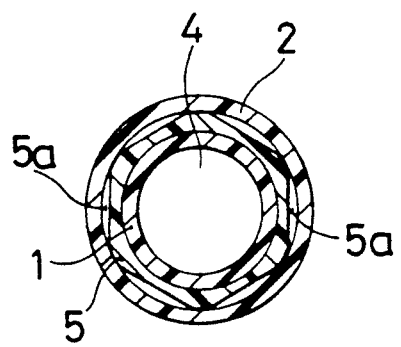

The distal end portion of the outer tube 2 is fixed to the inner tube 1 in such a manner that the second lumen 6 is not blocked. More specifically, the outer tube 2 is fixed to the inner tube 1 at a position a certain distance from its distal end toward the proximal side by a fixing member 5 as shown in FIG. 1 and in FIG. 2 which is a cross-sectional view taken along the line I—I in FIG. 1. In this embodiment, the outer and inner tubes 1 and 2 are fixed by means of a fixing member 5. The fixing member 5 has a cut 5a through which the second lumen 6 and the inside of the dilatation element 3 communicate. By thus fixing the distal end portion of the outer tube 2 to the inner tube 1, a slight displacement between the outer and inner tubes during insertion into vessels can be prevented and consequently a result the deformation of the folded dilatation element caused by the dislocation can also be suppressed. The fixing member 5 is welded to the outer and inner tubes by heat, ultrasonic wave or adhesives. Therefore, the material suitable for the fixing member 5 is easily welded to the materials of the outer and inner tubes. Preferably the fixing member 5 has about the same inner diameter as the outer diameter of the inner tube 1 and about the same outer diameter as the inner diameter of the outer tube 2. The lengthwise dimension of the fixing member 5 is 1 to 10 mm, preferably 2 to 8 mm. Materials usable for the fixing member 5 vary depending on the materials used for the inner and outer tubes and when the inner and outer tubes are formed of the polyolefin material, for example, EVA (ethylene vinyl acetate) is preferable. The ratio of the unbroken part of the fixing member 5 to the whole circumference is greater than $\frac{1}{3}$, preferably greater than $\frac{1}{2}$, more preferably 0.5 to 0.95, and most preferably 0.6 to 0.93. With the ratio within this range, the fixing member 5 does not substantially block the communication between the second lumen 6 and the inside of the dilatation element 3 and can securely fix the outer and inner tubes. The shape of the fixing member 5 is not limited to a broken ring as shown in FIG. 2, but may be triangular, rectangular, polyangular such as hexagonal as shown in FIG. 8, gear-like as shown in FIG. 7 or flat.

The distal end portion of the outer tube 2 is preferably tapered as shown in FIG. 1 and the distal end is preferably not fixed to the inner tube 1. By this construction, concentration of the stress to the portions where the inner tube 1 and outer tube 2 are fixed to each other by the fixing member 5 and hence the kinking of the catheter caused by the concentration of the stress can be prevented.

The outer tube has an outside diameter from 0.50 to 4.30 mm, preferably 0.60 to 4.00 mm and an inside diameter ranging from 0.40 to 3.80 mm, preferably 0.50 to 3.00 mm.

The material preferable for forming the outer tube 2 has a certain amount of flexibility. Materials usable for the outer tube 2 include thermoplastic resins such as polyolefin (polyethylene, polypropylene, ethylene-propylene copolymer, ethylene-vinyl acetate copolymer, etc.), polyvinyl chloride, polyamide elastomer and polyurethane. Of the above materials, the olefin resins are particularly preferable.

It is desirable to dispose a rigidity-imparting member 13 in the second lumen 6. The rigidity-imparting member 13 extends in the second lumen 6 formed between the inside surface of the outer tube 2 and the outside surface of the inner tube 1 from the proximal end of the catheter to near the distal end of the outer tube 2. This rigidity-imparting member 13 prevents too-sharp curving at bends in vessels and winding in vessels of the catheter and thereby makes it easy to fixing member the catheter tip into stenotic sections, without reducing the flexibility of the catheter.

The rigidity-imparting member 13 is preferably made of a wire material. A preferable wire material is metal wire with a diameter of 0.05 to 1.50 mm, preferably from 0.10 to 1.00 mm. Preferable metal wire is wire of resilient metals such as stainless steel and super elastic alloys. Wire of high tensile-strength stainless spring steel, super elastic alloys, for example, Ni-Ti alloy, and Cu-Al-Ni alloy is especially preferable. It is desirable that the rigidity-imparting member 13 is secured at the proximal portion and left free at both middle and distal portions. Not secured at the distal and middle portions, the rigidity-imparting member 13 can slide in the second lumen 6 and does not reduce the flexibility of the distal end of the catheter. By disposition of such a rigidity-imparting member 13, winding of the catheter in vessels can be suppressed. As a result, thrust force applied from the proximal region of the catheter is transmitted up to the distal end without being absorbed by bending parts. Thus manipulation of the catheter, particularly insertion of the distal end of the catheter (portion at which the dilatation element is attached) into stenotic sections is made much easier and it becomes possible to fixing member the distal end even into serious stenotic sections (sub-total obliteration) in blood vessels.

Figure 4:
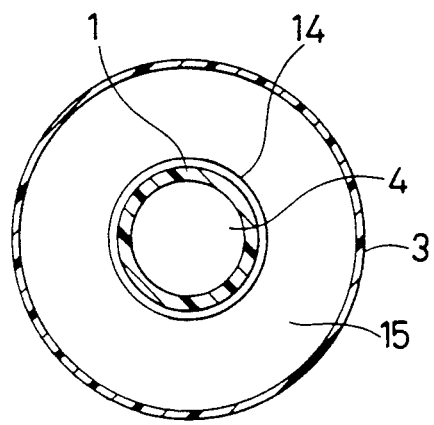
FIG. 4 is a cross-sectional view taken along the line II—II in FIG. 1.

The dilation element 3 is foldable and is folded together on the outer circumference of the inner tube 1 when it is deflated. The dilatation element 3 has a substantially cylindrical portion 3a of an approximately uniform diameter. The portion 3a must not necessarily be a complete cylinder, but may be polygonal in cross section as far as a part of it is substantially cylindrical. The front end portion 7 and rear end portion 8 of the dilatation element 3 are attached to the distal end portion of the inner tube 1 and that of the outer tube 2, respectively, in a liquid-tight seal by means of an adhesive or heating. When the distal end portion of the outer tube 2 is tapered as shown in FIG. 1, the rear end 8 of the dilatation element 3 may be attached to the tapered portion. A hollow space 15 is formed between the inner surface of the dilatation element 3 and the outer surface of the inner tube 1 as shown in FIG. 4 which is a cross-sectional view taken along the line II—II in FIG. 1. At the region near the rear end, the hollow space 15 is in communication with the second lumen 6 through the cut 5a in the fixing member 5.

The material preferable for the dilatation element 3 has a certain amount of flexibility. Materials usable for the dilatation element 3 include thermoplastic resins such as polyolefin (polyethylene, polypropylene, ethylene-propylene copolymer, ethylene-vinyl acetate copolymer, cross-linked ethylene-vinyl acetate copolymer, etc.), polyvinyl chloride, polyamide elastomer, polyurethane and polyester. Of the above materials, thermoplastic resins are preferable, polyester is more preferable, and polyethylene terephtalate is especially preferable.

The dilatation element 3 has tapered portions between the front end of the cylindrical portion 3a and the attached portion 7 to the inner tube 1 and between the rear end of the cylindrical portion 3a and the attached portion 8 to the outer tube 2. The dilatation element 13 has an outside diameter at the cylindrical region 3a ranging from 1.00 to 35.00 mm, preferably from 1.50 to 30.0 mm and a length of the same ranging from 3.00 to 80.00 mm, preferably from 10.00 to 75.0 mm, and an overall length of 5.00 to 120.00 mm, preferably 15.00 to 100.0 mm.

It is desirable to dispose a reinforcing member 14 around the outside surface of the inner tube 1. The reinforcing member 14 is preferably made of a coil spring. By using a reinforcing member in the form of a coil spring, kinking and collapsing of the inner tube 1 within the dilatation element 3 at bends in vessels can be prevented. The flexural rigidity of this region is much increased by tightly fitting a reinforcing member made of a single coil spring around the outside surface of the inner tube 1. The cross-section of the wire material for the reinforcing member 14 may be circular, elliptic, square or of any other appropriate shapes. It is desirable that the reinforcing member 14 extends over the length of the inner tube 1 from a position behind and near the portion where the dilatation element 3 is attached to the inner tube 1 to a position in front of and near the portion where the dilatation element 3 is attached to the outer tube 2, that is, the reinforcing member 14 has about the same length as the cylindrical portion 3a of the dilatation element 3 and is placed at the same position as the cylindrical portion 3a. By this construction, the reinforcing member 14 can also be used as a marker. In order to facilitate monitoring the position of the dilatation element 3 through a fluoroscope, it is preferable that the reinforcing member 14 is made of a X-ray opaque material impervious or only slightly pervious to radiation such as gold, platinum, tungsten, their alloys and sliver-palladium alloy and the reinforcing member 14 is densely wound in the regions of 0.5 to 4 mm, preferably 1 to 2 mm from its front and rear ends. The reinforcing member 14 is preferably secured in between the inner tube 1 and the tapered end portion of the outer tube 2. By this configuration, the reinforcing member 14 can be firmly fixed.

The branched hub 20 comprises a inner-tube hub 22 and a outer-tube hub 23. The inner-tube hub 22 is attached to the inner tube 1 and provided with a first opening 9 which communicates with the first lumen 4 and serves a guide wire port. The outer-tube hub 23 is attached to the outer tube 2 and provided with a second opening 11 which communicates with the second lumen 6 and serves as an injection port. The inner-tube hub 22 and outer-tube hub 23 are connected together into one body.

Figure 6:
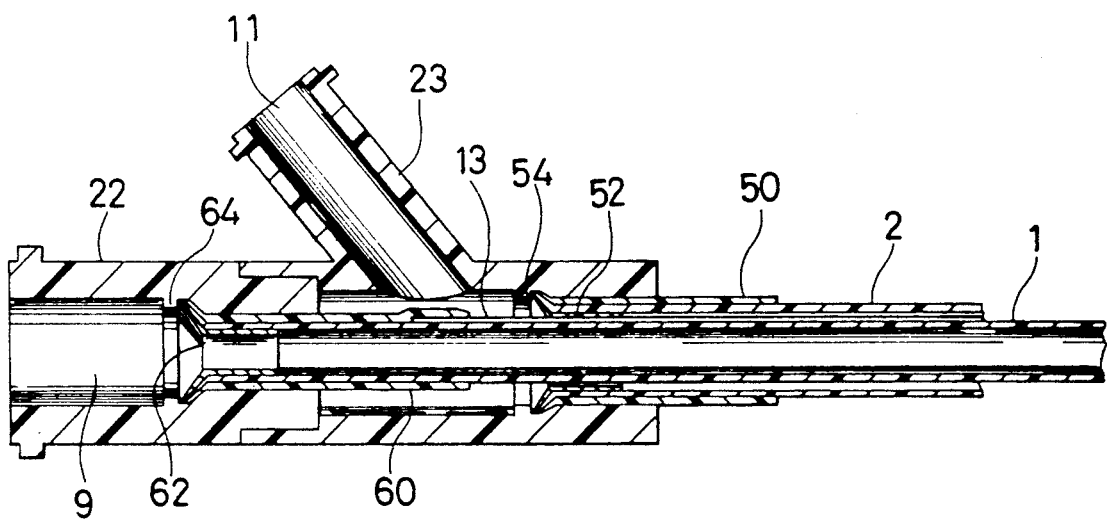
FIG. 6 is a cross-sectional view of the proximal region of an embodiment of the catheter equipped with a dilatation element according to the present invention.

FIG. 6 shows a cross section of an embodiment of the branched hub 20. In this embodiment, a kinking-prevention tube 50 is fitted over the proximal end of the outer tube 2. The outer tube 2 is secured to the outer-tube hub 23 by means of a clamping member 52 along with the kinking-prevention tube 50. The outer tube 2 may also be secured to the outer-tube hub 23 by applying an adhesive between the surfaces of the outer-tube hub 23 and the kinking-prevention tube 50. The materials preferable for the outer-tube hub 23 are thermoplastic resins such as polycarbonate, polyamide, polysulfone, polyacrylate, and methacrylate-butylene-styrene-copolymer.

A kinking-prevention tube 60 is fitted over the proximal end of the inner tube 1. The proximal end portion of the rigidity-imparting member 13 is secured by the kinking-prevention tube 60 to the outside surface of the inner tube 1. The proximal end portion of the rigidity-imparting member 13 must not necessarily be secured. The inner tube 1 is secured to the inner-tube hub 22 by means of a clamping member. 62 along with the kinking-prevention tube 60. The inner tube 1 may also be secured to the inner-tube hub 22 by applying an adhesive between the surfaces of the inner-tube hub 22 and the kinking-prevention tube 60. The materials preferable for the inner-tube hub 22 are thermoplastic resins such as polycarbonate, polyamide, polysulfone, polyacrylate, and methacrylate-butylene-styrene-copolymer. The inner-tube hub 22 and outer-tube hub 23 are connected in the manner as shown in FIG. 6. Instead of the branched hub 20, for example, it is also possible to connect tubes to the proximal ends of the inner and outer tubes 1 and 2 in a liquid-tight seal so that the tubes communicate with the first and second lumens 4 and 6 and then attach port members provided with an opening at the rear end to the tubes.

Next, the method for manufacturing the catheter of the present invention is described with reference to the drawings.

In this embodiment, the process comprises a step for making the inner tube 1 which has a lumen extending through from the distal end to the proximal end; a step for making the outer tube 2 which is a predetermined length shorter than the inner tube 1 and has a lumen extending through from the distal end to the proximal end and whose inner diameter is greater than the outside diameter of the inner tube; a step for making the dilatation element 3 which has the front end 7 and rear end 8 and is contractible or foldable; a step for inserting the inner tube 1 through the outer tube 2 and fixing the portion near the distal end of the outer tube 2 to the inner tube 1; a step for attaching the rear end 8 of the dilatation element 3 to the distal end portion of the outer tube 2; and a step for attaching the front end 7 of the dilatation element 3 to the distal end portion of the inner tube 1.

Each step will be described below taking the embodiment of the catheter quipped with a dilatation element shown in FIG. 1 as an example.

In the step for making the inner tube 1, inner tubes are made by forming a tube of one of the aforementioned thermoplastic resins preferable for the inner tube 1 by means of extrusion molding and then cutting the tube into a predetermined length or by injection molding.

In the step for making the outer tube 2, outer tubes are made by the same method as the inner tube 1.

In the step for making the dilatation element 3, dilatation elements are made by the process described below.

First, a thermoplastic-resin tube is formed of one of the aforementioned thermoplastic resins which has a certain amount of flexibility and thereby suitable for the dilatation element 3. This tube is put in a mold which has a hollow space formed in the shape of the dilatation element in its expanded state. The lumen of the tube is clamped in air-tight seal near one end and the tube is pulled tight by the tube holder to eliminate the slack of the tube. The portion of the tube at which a dilatation element is to be formed is heated by a heater up to a temperature beyond the second order glass transition point (Tg) and the heated portion is inflated and pressed against the inner surface of the mold by introducing a gas under pressure. After the tube has cooled down, the mold is removed and both end portions of the tube are cut off from the dilatation element.

This step for making the dilatation element can be executed independently of the steps for forming the inner and outer tubes and put in any order with respect to those steps.

Next described is the step for providir roximal end portion of the outer tube 2 with an opening 11 communicating with the lumen 6 of the outer tube 2.

It is desirable that the opening 11 is provided by means of an outer-tube hub 23 with an opening attached to the proximal end of the outer tube 2. The procedure for the embodiment shown in FIG. 6 is described below.

First, the kinking-prevention tube 50 is secured to one end portion of the outer tube 2. To secure to the outer tube 2, the kinking-prevention tube 50 is formed of a heat shrinkable material in such a thickness that the inner diameter becomes a little smaller than the outer diameter of the outer tube 2 by shrinkage. This kinking-prevention tube 50 is put on an end portion of the outer tube 2 and heated by blowing hot air, for example, to cause it to shrink.

Then the outer-tube hub 23 is attached to this proximal end portion of the outer tube 2 reinforced with the kinking-prevention tube 50. The outer-tube hub 23 is secured by inserting a clamping member 52 having about the same outer diameter as the inner diameter of the outer tube 2 and a flared end into the proximal end of the outer tube 2, next inserting the outer tube 2 from the distal end into the outer-tube hub 23 from the rear end side of the hub 23, and then Pushing the clamping member 52 together with the outer tube 2 until the flared end of the clamping member 52 passes over a projection 54 provided in the inner surface of the outer tube 2. The outer-tube hub 23 may be secured by applying an adhesive between the inner surface of the outer-tube hub 23 and the outer surface of the kinking-prevention tube 50. The materials suitable for the outer-tube hub are thermoplastic resins such as polycarbonate, polyamide, polysulfone, polyacrylate, and methacrylate-butylene-styrene-copolymer.

This step for providing the proximal end portion of the outer tube 2 with an opening 11 communicating with the lumen 6 of the outer tube 2 can be executed at any time after the step for making the outer tube 2. It is preferable to execute this step after the step for attaching the rear end of the dilatation element 3 to the distal end portion of the outer tube 2 hereinafter described. This step may be disposed in any order with respect to the step for forming the inner tube 1.

Next described is the step for providing the proximal end portion of the inner tube 1 with an opening 9 communicating with the lumen 4 of the inner tube 1.

It is desirable that the opening 9 is provided by means of an inner-tube hub 22 with an opening 9 attached to the proximal end of the inner tube 1. The procedure for the embodiment shown in FIG. 6 is described below.

First, the kinking-prevention tube 60 is secured to one end portion of the inner tube 1. To secure to the inner tube 1, the kinking-prevention tube 60 is formed of a heat shrinkable material in such a thickness that the inner diameter becomes a little smaller than the outer diameter of the inner tube 1 by shrinkage. This kinking-prevention tube 60 is put on an end portion of the inner tube 1 and heated by blowing hot air, for example, to cause it to shrink. In the embodiment shown in FIG. 6, the rigidity-imparting element 13 is disposed between the inner tube 1 and the outer tube 2. The proximal end portion of the rigidity-imparting element 13 can be secured simultaneously with fixing of the kinking-prevention tube 60 to the inner tube 1 by putting its end between the kinking-prevention tube 60 and the inner tube 1 as shown in FIG. 6 and heating the tube 60.

Then the inner-tube hub 22 is attached to this proximal end portion of the inner tube 1 reinforced with the kinking-prevention tube 60. The inner-tube hub 22 is secured by inserting a clamping member 62 having about the same outer diameter as the inner diameter of the inner tube 1 and a flared end into the proximal end of the inner tube 1, next inserting the inner tube 1 from the distal end into the inner-tube hub 22 from the rear end side of the hub 22, and then pushing the clamping member 62 together with the inner tube 1 until the flared end of the clamping member 62 passes over a projection 64 Provided in the inner surface of the inner tube 1. The inner-tube hub 22 may be secured by applying an adhesive between the inner surface of the inner-tube hub 22 and the outer surface of the kinking-prevention tube 60. The materials suitable for the inner-tube hub are the same as for the outer-tube hub.

This step for providing the proximal end portion of the inner tube 1 with an opening 9 communicating with the lumen 4 of the inner tube 2 can be executed at any time after the step or making the inner tube 1. This step may be disposed in any order with respect to the steps for forming the outer tube 2, providing the proximal end of the outer tube 2 with the second opening 11 communicating with the lumen 6 of the outer tube 2, and making the dilatation element 3.

Then the inner-tube hub 22 and the outer-tube hub 23 are connected together by the following procedure.

As shown in FIG. 6, the inner tube 1 is inserted from the distal end into the outer-tube hub 23 from the rear end side of the hub 23 and the front end portion of the inner-tube hub 2 is then fitted into the rear end of the outer-tube hub 23. To prevent the inner tube 1 from kinking during this handling, it is desirable to insert a mandrel through the inner tube 1. The inner-tube hub 22 and the outer-tube hub 23 can be securely connected by applying an adhesive to the surfaces to contact with each other.

This step for connecting the inner-tube hub 22 and the outer-tube hub 23 may be executed at any time after the steps for making the inner tube 1 and attaching the inner-tube hub 22 to the proximal end of the inner tube 1 and for making the outer tube 2 and attaching the outer-tube hub 23 to the proximal end of the outer tube 2.

Figure 9:
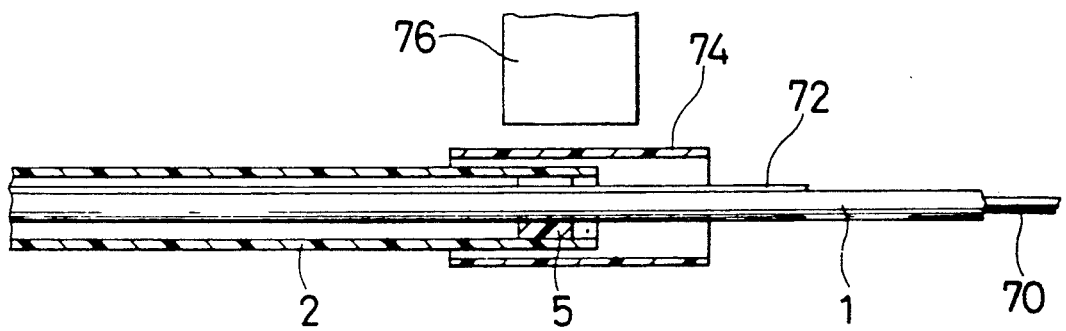
FIGS. 9 and 10 illustrate the steps for fixing the outer and inner tubes in the manufacturing process of the catheter equipped with a dilatation element according to the present invention.
Figure 10:
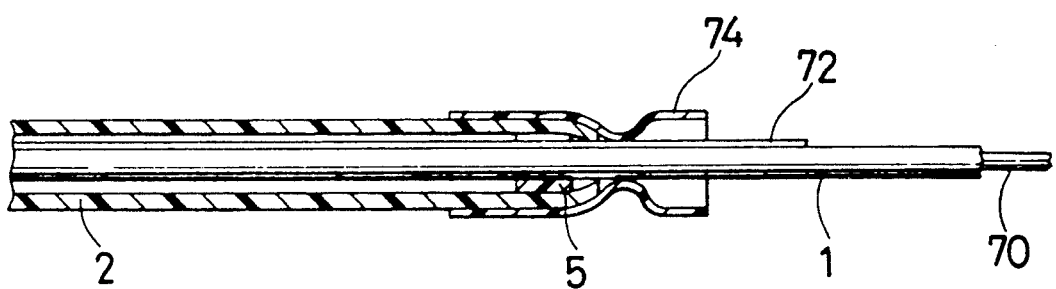

Next described is the step for attaching a portion near the distal end of the outer tube 2 to the inner tube 1 with reference to FIGS. 9 and 10.

The fixing member 5 is formed of a material which can be welded to the inner tube 1 and the outer tube 2 in the shape of a ring with a partial cut 5a. On the other hand, the inner tube 1 with a mandrel 70 inserted through is inserted into the outer tube 2. The fixing member 5 is put on the distal end of the inner tube 1 and pushed into between the inner tube 1 and the outer tube 2 to the position a certain distance from the distal end of the outer tube toward the proximal end, where both tubes are to be fixed together. A mandrel 72 for preventing the cut 5a from being filled up is inserted into the outer tube 2 from either distal or proximal end and passed through the cut 5a. An appropriate number of mandrels may be used according to the size and number of the cuts in the fixing member 5. Further, a heat shrinkable tube 74 is put on the outer tube 2 over the region around the position where the outer tube is fixed to the inner tube 1. It is desirable that the tube 74 is made of a material such as heat shrinkable silicone tube which is not welded to the inner and outer tubes 1 and 2. This setting is shown in FIG. 9. Then the heat shrinkable tube 74 is partially heated by a heater 76 so that only a part of the tube 74 shrinks and the fixing member 5 is welded to the inner and outer tubes 1 and 2. Since the mandrel 72 is passed through the cut 5a, a passage is left open after the mandrel 72 is pulled out and thus blockage of the space between the inner and outer tubes 1 and 2 is prevented when the fixing member is melted. Further, by using the heat shrinkable tube 74, it is possible to fix the inner and outer tubes 1 and 2 and taper the distal end of the outer tube 2 simultaneously.

Next described is the step for attaching the rear end 8 of the dilatation element 3 to the distal end portion of the outer tube 2.

First, a mandrel having an outer diameter equal to or a little smaller than the inner diameter of the inner tube 1 is inserted into the inner tube 1 from either distal or proximal end. Next, an appropriate amount of an adhesive is applied to the portion near the distal end of the outer tube 2 where the rear end portion 8 of the dilatation element 3 is to be attached. Then the dilatation element 3 is put o the distal end of the mandrel and slid on the distal end portion of the outer tube 2 so that the front side end of the rear end portion 8 is about the same position as the distal end of the outer tube 2. There the rear end portion 8 of the dilatation element 3 is bonded to the outer tube 2 by the adhesive. Heating and curing may be used as necessary.

To increase the strength of bonding between the outer tube and the dilation element, it is preferable to apply surface treatments such as corona discharge to the distal end portion of the outer tube 2.

The step for attaching the front end portion 7 of the dilation element 3 to the distal end portion of the inner tube 1 is described below.

First, a mandrel having an outer diameter equal to or a little smaller than the inner diameter of the inner tube 1 is inverted into the inner tube 1 from either distal or proximal end as in the step for attaching the rear end portion of the dilatation element 3 to the distal end portion of the outer tube 2. In previous steps, the dilatation element 3 is attached to the outer tube 2, the inner tube 1 is put in the outer tube 2, and the inner-tube hub 22 and the outer-tube hub 23 are connected together. The front end of the dilatation element 3 extends beyond the distal end of the inner tube 1. Next, an appropriate adhesive is applied to the portion near the distal end of the inner tube 1 where the front end portion of the dilatation element 3 and heated and cured. The front end portion of the dilatation element 3 is then bonded to the distal end Portion of the inner tube 1. To increase the strength of bonding between the dilatation element and the inner tube, it is preferable to apply surface treatments such as corona discharge to the distal end portion of the inner tube 1. It is also preferable to put a glass mold on the front end 7 from the distal end of the mandrel, heat the glass mold by a heater, and bond the front end 7 so as to surrounds the distal end portion of the inner tube 1.

Molding of the distal end portion is easily made by inserting the distal end of the inner tube into a mold (glass mold, metal mold, etc.) with an inner surface formed in a desired shape and heating the mold to melt the end of the inner tube into the shape of the mold.

The operation of the catheter according to the present invention is described below using embodiments shown in FIGS. 1 to 6 with reference to FIGS. 11 to 15.

It is desirable to remove the air in the catheter equipped with a dilatation element as completely as possible before treating stenosis of blood vessels by dilating the stenotic sections. Therefore, a suction and injection means such as a syringe is attached to the second opening 11 of the catheter and charged with a liquid such as X-ray contrast medium to repeat suction and injection. Thus, the air in the second lumen and the dilatation element is substituted by the contrast medium and removed.

Figure 12:
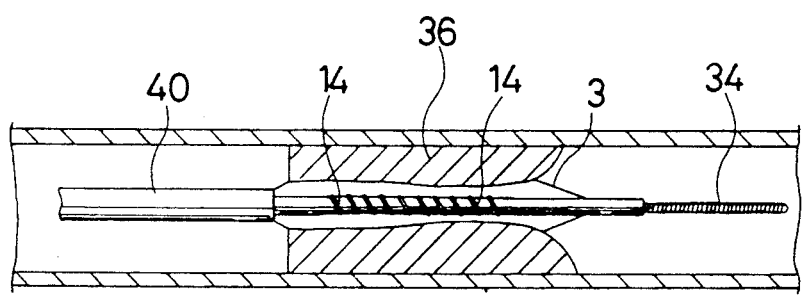
Figure 13:
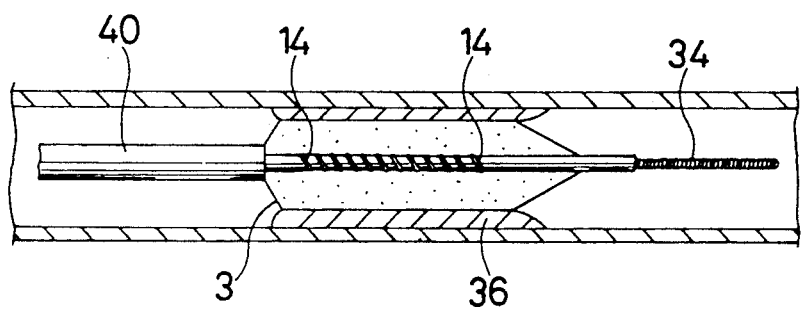
Figure 14:
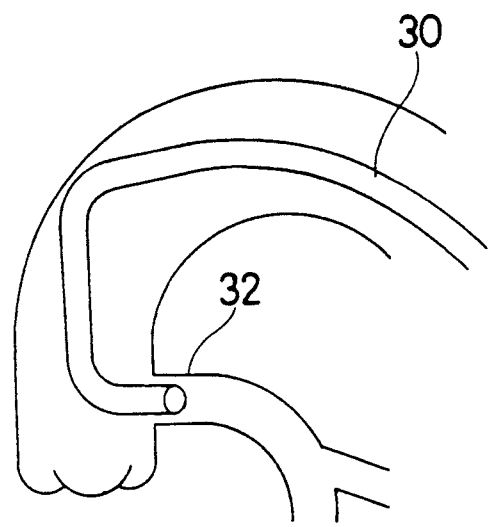
Figure 15:
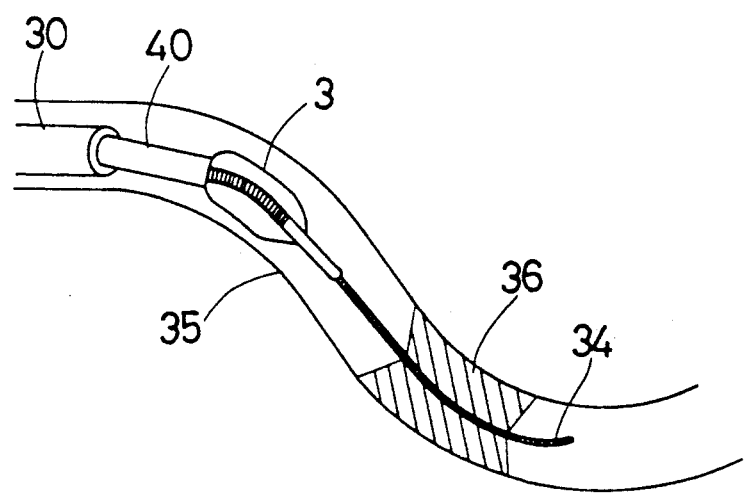

Before the catheter equipped with a dilation element 40 is inserted, blood vessels are first determined by means of the Seldinger method or other methods and a guide-catheter guide wire (not shown) is left in the vessels. Next, a guide catheter 30 is inserted into the vessels along the guide wire and engaged in the ostium 32 of the coronary artery which has the target lesion as shown in FIG. 14. Then guide-catheter guide wire is pull out. After the guide catheter 30 is engaged in the ostium 32, the catheter equipped with a dilation element 40 through which a guide wire 34 is inserted to extend several centimeters out of the distal end of the catheter is inserted from the Y-shaped connector 50 at the proximal end of the guide catheter into the guide catheter as shown in FIG. 1. The catheter 40 advances in the guide catheter 30 and enters from the distal end of the guide catheter into the vessel 35 which has the target lesion as shown in FIG. 15. After that, the guide wire 34 is advanced toward the target lesion, passed through the stenotic section 36, and left in the vessel. Next, the catheter 40 is advanced in the vessel 35 along the guide wire 34. When the catheter 40 reaches the stenotic section, the dilatation element 3 is positioned in the stenotic section as shown in FIG. 12 monitoring the position of the X-ray opaque maker 14 provided on the inner tube 1 through a fluoroscope. After the dilatation element 3 is properly positioned, a vasographic contrast medium is injected at a pressure from several atmospheres to ten and several atmospheres by means of the injector 54 equipped with a pressure gauge which is connected to the second opening serving as the injection port of the catheter 40. Thus the dilatation element 3 is expanded to dilate the stenotic section 36 as shown in FIG. 13. The blood stream in the peripheral vessels is checked by injecting vasographic contrast medium from the injection port 52 of the Y-shaped connector 50 of the guide catheter 30. If the improvement of the blood stream is recognized, the catheter 40 is withdrawn with the guide wire 34, the guide catheter is pulled out, and finally achieve hemostasis by tuncture site compression.

Since the catheter equipped with a dilatation element of the present invention comprises an inner tube having a first lumen open at the distal end, an outer tube which surrounds the inner tube so that a predetermined length of the distal end of the inner tube extends out of the distal end of the outer tube and a second lumen is formed between the inner surface of the outer tube and the outer surface of the inner tube, a foldable dilatation element which has the front and rear end portions attached to the inner tube and the outer tube respectively and whose internal space communicates with the second lumen, a first opening which communicates with the first lumen at the proximal end of the inner tube; a second opening which communicates with the second lumen at the proximal end of the outer tube, a fixing member inserted between the outer tube and the inner tube at a position a certain distance from the distal end of the outer tube toward the proximal end, the outer tube is fixed to the inner tube without blocking the second lumen by the fixing member, and the distal end portion of the outer tube is not fixed to the inner tube, it can prevent the slight difference in the forward movement of the outer and inner tubes while being inserted into vessels and hence the expansion of the outer diameter of the dilatation element caused by the displacement between both tubes though it is a coaxial-type catheter whose inner and outer tubes are disposed coaxial. As a resulting advantage, the catheter of the present invention is much easier to manipulate, particularly to insert the dilatation element of the catheter into stenotic sections. And concentration of the stress to the portions where the inner tube and outer tube are fixed to each other by the fixing member and hence the kinking of the catheter caused by the concentration of the stress can be prevented.

What is claimed is:

1. A catheter equipped with a dilatation element comprising, an inner tube having a first lumen open at the distal end;

an outer tube which surrounds the inner tube so that a predetermined length of the distal end of the inner tube extends out of the distal end of the outer tube and a second lumen is formed between the inner surface of the outer tube and the outer surface of the inner tube;

a foldable dilatation element which has the front and rear end portions attached to the inner tube and the outer tube respectively and whose internal space communicates with the second lumen;

a first opening which communicates with the first lumen at the proximal end of the inner tube; and a second opening which communicates with the second lumen at the proximal end of the outer tube;

a fixing member inserted between the outer tube and the inner tube at a position a certain distance from the distal end of the outer tube toward the proximal end thereof, the outer tube is fixed to the inner tube without blocking the second lumen by the fixing member, and the distal end portion of the outer tube is not fixed to the inner tube.

2. A catheter equipped with a dilatation element in claim 1, wherein a rigidity-imparting member made of a wire material and extending lengthwise is disposed in said second lumen.

3. A catheter equipped with a dilatation element in claim 2, wherein the distal end of said rigidity-imparting member is at the proximal side of said points where the outer and inner tube are fixed and left free.

4. A catheter equipped with a dilatation element in claim 1, wherein said fixing member has about the same inner diameter as the outer diameter of said inner tube and about the same outer diameter as said inner diameter of the outer tube and further, has at least one partial cut.

5. A catheter equipped with a dilatation element in claim 4, wherein said fixing member has the unbroken part of at least half of the whole circumference.

6. A catheter equipped with a dilatation element in claim 1, wherein said dilatation element has substantially cylindrical portion in its middle region and a reinforcing member is disposed around said inner tube at about the same lengthwise position as the cylindrical portion of said dilatation element.

7. A catheter equipped with a dilatation element in claim 6, wherein said reinforcing member is formed of a material substantially impervious to X-ray.

8. A catheter equipped with a dilatation element in claim 6, wherein said reinforcing member is in the form of a coil of a wire material wound around said inner tube.

9. A catheter equipped with a dilatation element in claim 8, wherein said wire material is densely wound at both end portions of said reinforcing member in the form of a coil.

10. A catheter equipped with a dilatation element in claim 1, wherein the distal end portion of said outer tube is tapered.

11. A catheter equipped with a dilatation element in claim 1, wherein the distal end of said outer tube is tapered and not fixed and the rear portion of said reinforcing member is held between the distal end portion of said outer tube and said inner tube.

* * * * *

UNITED STATES PATENT AND TRADEMARK OFFICE
CERTIFICATE OF CORRECTION

PATENT NO. : 5,176,637
DATED : January 5, 1993
INVENTOR(S) : Kyuta Sagae It is certified that error appears in the above-identified patent and that said Letters Patent is hereby corrected as shown below:

```
Column 1, line 53, "o the" should be --of the--.

Column 7, line 46, "providir    roximal" should be
--providing the proximal--.

Column 8, line 3, "Pushing" should be --pushing--.

Column 8, line 57, "Provided" should be --provided--.

Column 9, line 9, "hub 2" should be --hub 22--.

Figure 11:
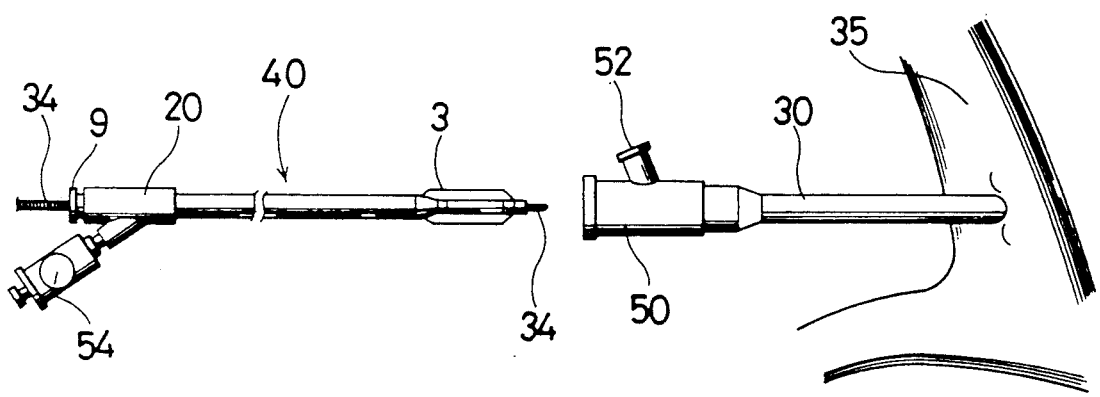
FIGS. 11 to 15 illustrate the function of the catheter equipped with a dilatation element according to the present invention.

Column 11, line 1, "Fig. 1." should be --Fig. 11.--.
```

Signed and Sealed this

Fifteenth Day of March, 1994

Attest:

BRUCE LEHMAN

*Attesting Officer*        *Commissioner of Patents and Trademarks*